United States Patent
Lu

(10) Patent No.: US 11,021,731 B2
(45) Date of Patent: Jun. 1, 2021

(54) ANALYTE SENSING LAYERS, ANALYTE SENSORS AND METHODS FOR FABRICATING THE SAME

(71) Applicant: MEDTRONIC MINIMED, INC., Northridge, CA (US)

(72) Inventor: Kelly Lu, Plymouth, MN (US)

(73) Assignee: MEDTRONIC MINIMED, INC., Northridge (CA)

( * ) Notice: Subject to any disclaimer, the term of this patent is extended or adjusted under 35 U.S.C. 154(b) by 169 days.

(21) Appl. No.: 16/111,057

(22) Filed: Aug. 23, 2018

(65) Prior Publication Data
US 2020/0063176 A1    Feb. 27, 2020

(51) Int. Cl.
| | |
|---|---|
| *C12Q 1/00* | (2006.01) |
| *A61B 5/1486* | (2006.01) |
| *A61B 5/145* | (2006.01) |
| *A61M 5/162* | (2006.01) |
| *A61M 5/158* | (2006.01) |
| *G01N 27/327* | (2006.01) |

(52) U.S. Cl.
CPC .......... *C12Q 1/006* (2013.01); *A61B 5/14532* (2013.01); *A61B 5/14865* (2013.01); *A61M 5/158* (2013.01); *A61M 5/162* (2013.01); *C12Q 1/003* (2013.01); *C12Q 1/005* (2013.01); *G01N 27/3271* (2013.01); *G01N 27/3273* (2013.01)

(58) Field of Classification Search
CPC ........ C12Q 1/006; C12Q 1/003; C12Q 1/005; G01N 27/3273; A61B 5/1486
See application file for complete search history.

(56) References Cited

U.S. PATENT DOCUMENTS

| | | | |
|---|---|---|---|
| 4,755,173 A | | 7/1988 | Konopka et al. |
| 5,380,620 A | * | 1/1995 | Namiki .................... B41M 1/00 430/252 |
| 5,391,250 A | | 2/1995 | Cheney, II et al. |
| 5,485,408 A | | 1/1996 | Blomquist |
| 5,522,803 A | | 6/1996 | Teissen-Simony |
| 5,665,065 A | | 9/1997 | Colman et al. |
| 5,800,420 A | | 9/1998 | Gross et al. |
| 5,807,375 A | | 9/1998 | Gross et al. |
| 5,925,021 A | | 7/1999 | Castellano et al. |
| 5,954,643 A | | 9/1999 | Van Antwerp et al. |
| 6,017,328 A | | 1/2000 | Fischell et al. |
| 6,175,752 B1 | * | 1/2001 | Say ...................... A61B 5/1486 600/345 |
| 6,186,982 B1 | | 2/2001 | Gross et al. |
| 6,246,992 B1 | | 6/2001 | Brown |
| 6,248,067 B1 | | 6/2001 | Causey, III et al. |
| 6,248,093 B1 | | 6/2001 | Moberg |
| 6,355,021 B1 | | 3/2002 | Nielsen et al. |

(Continued)

*Primary Examiner* — Luan V Van
*Assistant Examiner* — Caitlyn Mingyun Sun
(74) *Attorney, Agent, or Firm* — Shumaker & Sieffert, P.A.

(57) ABSTRACT

Analyte sensors and methods for fabricating analyte sensors and analyte sensing layers are presented here. In accordance with certain embodiments, a method for fabricating an analyte sensor includes providing a base layer and forming a conductive layer over the base layer. Further, the method includes forming an analyte sensing layer disposed over the conductive layer. The analyte sensing layer includes glucose oxidase entrapped within a thermally-cured polymer matrix and within a UV-cured polymer matrix.

21 Claims, 3 Drawing Sheets

(56) References Cited

U.S. PATENT DOCUMENTS

| | | | |
|---|---|---|---|
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,252,912 B2 * | 8/2007 | Kataoka | C08J 7/18 428/420 |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,364,229 B2 * | 1/2013 | Simpson | A61B 5/14532 600/345 |
| 9,937,495 B2 * | 4/2018 | Srinivas | B01L 3/502784 |
| 2007/0123819 A1 | 5/2007 | Mernoe et al. |
| 2010/0160861 A1 | 6/2010 | Causey, III et al. |
| 2015/0122645 A1 * | 5/2015 | Yang | A61B 5/14865 204/403.14 |
| 2018/0219164 A1 * | 8/2018 | Xu | B33Y 10/00 |

* cited by examiner

ANALYTE SENSING LAYERS, ANALYTE SENSORS AND METHODS FOR FABRICATING THE SAME

TECHNICAL FIELD

Embodiments of the subject matter described herein relate generally to analyte sensing layers for monitoring analyte levels in patients. More particularly, embodiments of the subject matter relate to glucose sensors, and to methods for fabricating glucose sensors.

BACKGROUND

The pancreas of a normal healthy person produces and releases insulin into the blood stream in response to elevated blood plasma glucose levels. Beta cells (β-cells), which reside in the pancreas, produce and secrete insulin into the blood stream as it is needed. If (β-cells become incapacitated or die, a condition known as Type 1 diabetes mellitus (or in some cases, if (β-cells produce insufficient quantities of insulin, a condition known as Type 2 diabetes), then insulin may be provided to a body from another source to maintain life or health.

Traditionally, because insulin cannot be taken orally, insulin has been injected with a syringe. More recently, the use of infusion pump therapy has been increasing in a number of medical situations, including for delivering insulin to diabetic individuals. For example, external infusion pumps may be worn on a belt, in a pocket, or the like, and they can deliver insulin into a body via an infusion tube with a percutaneous needle or a cannula placed in subcutaneous tissue.

As of 1995, less than 5% of Type 1 diabetic individuals in the United States were using infusion pump therapy. Currently, over 7% of the more than 900,000 Type 1 diabetic individuals in the U.S. are using infusion pump therapy. The percentage of Type 1 diabetic individuals that use an infusion pump is growing at a rate of over 2% each year. Moreover, the number of Type 2 diabetic individuals is growing at 3% or more per year, and growing numbers of insulin-using Type 2 diabetic individuals are also adopting infusion pumps. Additionally, physicians have recognized that continuous infusion can provide greater control of a diabetic individual's condition, so they too are increasingly prescribing it for patients.

An infusion pump system may include an infusion pump that is automatically and/or semi-automatically controlled to infuse insulin into a patient. The infusion of insulin may be controlled to occur at times and in amounts that are based, for example, on blood glucose measurements obtained from an embedded analyte sensor, such as a glucose sensor, in real-time.

Analyte sensors such as biosensors include devices that use biological elements to convert a chemical analyte in a matrix into a detectable signal. There are many types of biosensors used for a wide variety of analytes. The most studied type of biosensor is the amperometric glucose sensor, which is crucial to the successful glucose level control for diabetes.

A typical glucose sensor works according to the following chemical reactions:

Equation 1

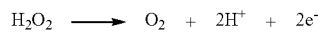

Equation 2

In equation 1, the glucose oxidase is used to catalyze the reaction between glucose and oxygen to yield gluconic acid and hydrogen peroxide ($H_2O_2$). The hydrogen peroxide reacts electrochemically as shown in equation 2 and the resulting current can be measured by a potentiostat. These reactions, which occur in a variety of oxidoreductases known in the art, are used in a number of sensor designs.

As analyte sensor technology matures and new applications for sensor technology are developed, there is a need for improved sensors for monitoring analyte levels in patients, and for improved methods for fabricating such sensors.

Accordingly, it is desirable to have an improved analyte sensing layer, and improved analyte sensor, and improved methods for fabricating analyte sensing layers and methods for fabricating analyte sensors that address the shortcomings of traditional sensor systems and methods. Furthermore, other desirable features and characteristics will become apparent from the subsequent detailed description and the appended claims, taken in conjunction with the accompanying drawings and the foregoing technical field and background.

BRIEF SUMMARY

A method for fabricating an analyte sensor is presented here. In accordance with certain embodiments, a method for fabricating an analyte sensor includes providing a base layer and forming a conductive layer over the base layer. Further, the method includes forming an analyte sensing layer disposed over the conductive layer. The analyte sensing layer includes glucose oxidase entrapped within a thermally-cured polymer matrix and within a UV-cured polymer matrix.

A method for fabricating an analyte sensing layer is also presented here. The method includes blending an enzyme, a polymer binder, a thermal cross-linker, a photo-initiator, and a monomer or oligomer including multifunctional acrylate to form a mixture. The method further includes thermally-curing the polymer binder and the thermal cross-linker by drying the mixture to form an intermediate film with a thermally-cured polymer matrix. Also, the method includes UV-curing the monomer or oligomer including multifunctional acrylate by exposing the intermediate film to UV light to form a UV-cured polymer matrix. In the analyte sensing layer, the enzyme is entrapped within the thermally-cured polymer matrix and within the UV-cured polymer matrix.

Also provided is an exemplary embodiment of an analyte sensor. The analyte sensor includes a base layer and a conductive layer over the base layer. Further, the analyte sensor includes an analyte sensing layer disposed over the conductive layer. The analyte sensing layer includes glucose oxidase entrapped within a thermally-cured polymer matrix and within a UV-cured polymer matrix.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description. Also, while the preceding background discusses glucose sensing and exemplary analyte sensors are described as glucose sensors herein, such description is for convenience and is not limiting. The claimed subject matter may include any type of analyte sensor utilizing an embodiment of the sensor electrodes described herein.

In an exemplary embodiment, an analyte sensing layer is formed as a single layer overlying the electrode and includes an enzyme, components for immobilizing the enzyme, and components for regulating analyte contact with the enzyme. In particular embodiments, a method for forming an analyte sensing layer includes a dual cure process in which certain components are thermally cured before other components are cured by exposure to ultraviolet (UV) radiation or light, i.e., UV-cured. As a result, the enzyme is entrapped by both a thermally cured matrix and a UV-cured matrix. As used herein, the terms "thermal cure" and "thermal curing" refer to a change in state, condition, and/or structure in a material that is induced by increased temperature. As used herein, the terms "UV cure" and "UV curing" refer to a change in state, condition, and/or structure in a material that is induced by UV radiation. As used herein, a "thermal cross-linker" is a compound that only upon thermal treatment, i.e., heating, links one polymer chain to another. As used herein a "UV photo-initiator" is a molecule that creates reactive species (free radicals, cations or anions) when exposed to UV radiation to initiate a photopolymerization process, where monomer or oligomer molecules react to form polymer chains or three-dimensional networks.

According to certain embodiments, examples of analyte sensors and/or analyte sensing layers as described herein may be implemented in a hospital environment to monitor levels of glucose in a patient. Alternatively, according to certain embodiments, examples of analyte sensors and/or analyte sensing layers as described herein may be implemented in non-hospital environments to monitor levels of glucose in a patient. Here, a patient or other non-medical professional may be responsible for interacting with an analyte sensors and/or analyte sensing layers.

Figure 1:
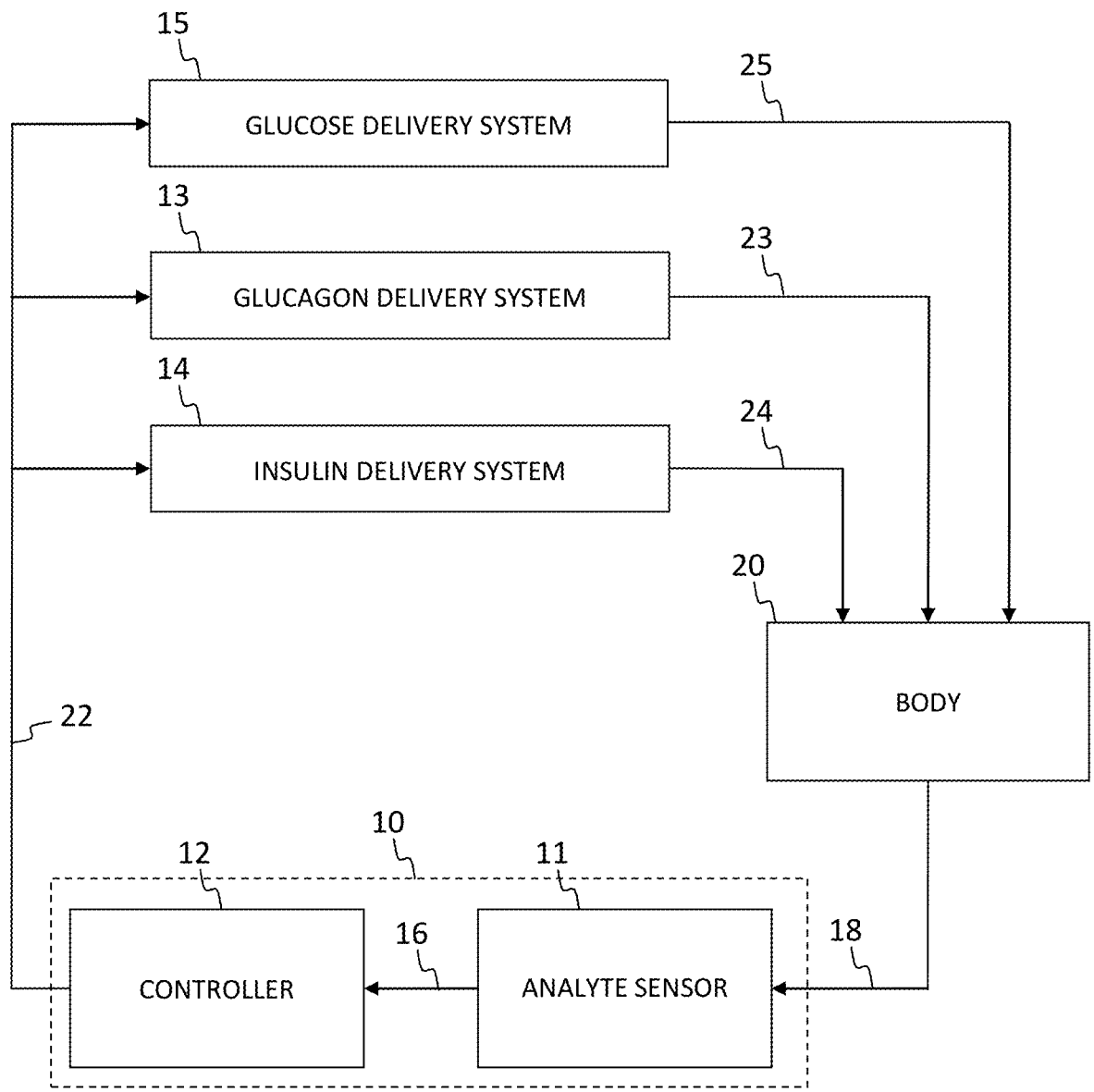
FIG. 1 is a block diagram of an analyte monitoring apparatus in accordance with an embodiment.

FIG. 1 is a block diagram of an example analyte monitoring apparatus 10 for use with a glucose control system in accordance with an embodiment. Particular embodiments of the analyte monitoring apparatus 10 may include an analyte sensor 11, including an analyte sensing layer, and a controller 12. The analyte monitoring apparatus 10 is provided for use with an insulin delivery system 14, a glucagon delivery system 13, and a glucose delivery system 15, as shown in FIG. 1. The analyte monitoring apparatus 10 may be considered to include the insulin delivery system 14, glucagon delivery system 13, and glucose delivery system 15.

In certain exemplary embodiments, analyte sensor 11 may generate a sensor signal 16 representative of blood glucose levels 18 in body 20, and it may provide sensor signal 16 to controller 12. Controller 12 may receive sensor signal 16 and generate commands 22 that are communicated to insulin delivery system 14, glucagon delivery system 13, and/or glucose delivery system 15. Insulin delivery system 14 may receive commands 22 and infuse insulin 24 into body 20 in response to commands 22. Likewise, glucagon delivery system 13 may receive commands 22 and infuse glucagon 23 into body 20 in response to commands 22. Similarly, glucose delivery system 15 may receive commands 22 and provide glucose 25 into body 20 in response to commands 22.

Analyte sensor 11 may include a glucose sensor, sensor electrical components to provide power to a sensor and to generate sensor signal 16, a sensor communication system to carry sensor signal 16 to controller 12, and a sensor system housing for electrical components and a sensor communication system. A glucose sensor may measure blood glucose directly from a blood stream, indirectly via interstitial fluid using, e.g., a subcutaneous sensor, some combination thereof, and so forth, just to name a few examples. As used herein, "blood glucose", "measured blood glucose", "blood glucose concentration", "measured blood glucose concentration", and the like may refer to a glucose level, a blood glucose level, a blood glucose concentration, and so forth that has been obtained via any type of glucose sensor. It should be understood, however that using a blood glucose sensor is only one particular technique for obtaining such observations or measurements, and that other techniques, such as measuring blood glucose inform observations of other body fluids (e.g., observations of the presence of glucose in interstitial fluid using a subcutaneous sensor), may be used without deviating from claimed subject matter.

Controller 12 may include electrical components and software to generate commands 22 for insulin delivery system 14, glucagon delivery system 13, and/or glucose delivery system 15 based on sensor signal 16. Controller 12 may also include a controller communication system to receive sensor signal 16 and provide commands 22 to insulin delivery system 14, glucagon delivery system 13, and/or glucose delivery system 15. In particular example implementations, controller 12 may include a user interface and/or operator interface (not shown) including a data input device and/or a data output device. Such a data output device may, for example, generate signals to initiate an alarm and/or include a display or printer for showing status of a controller 12 and/or a patient's vital indicators. Such a data input device may include dials, buttons, pointing devices, manual switches, alphanumeric keys, a touch-sensitive display, combinations thereof, and/or the like for receiving user and/or operator inputs. Such a data input device may be used for scheduling and/or initiating insulin bolus injections for meals, for example. It should be understood, however, that these are merely examples of input and output devices that may be a part of an operator and/or user interface and that claimed subject matter is not limited in these respects.

Insulin delivery system 14 may include an infusion device and/or an infusion tube to infuse insulin 24 into body 20. Similarly, glucagon delivery system 13 may include an infusion device and/or an infusion tube to infuse glucagon 23 into body 20. Likewise, glucose delivery system 15 may include an infusion device and/or an infusion tube to infuse glucose 25 into body 20. In alternative embodiments, insulin 24, glucagon 23, and/or glucose 25 may be infused into body 20 using a shared infusion tube. In other alternative embodiments, insulin 24, glucagon 23, and/or glucose 25 may be infused using an intravenous system for providing fluids to a patient (e.g., in a hospital or other medical environment). It should be understood, however, that certain example embodiments may include an insulin delivery system 14 without a glucagon delivery system 13 and/or without a glucose delivery system 15.

In particular embodiments, an infusion device (not explicitly identified in FIG. 1) may include infusion electrical components to activate an infusion motor according to commands 22, an infusion communication system to receive commands 22 from controller 12, and an infusion device housing (not shown) to hold the infusion device.

In particular embodiments, controller 12 may be housed in an infusion device housing, and an infusion communication system may include an electrical trace or a wire that carries commands 22 from controller 12 to an infusion device. In alternative embodiments, controller 12 may be housed in a sensor system housing, and a sensor communication system may include an electrical trace or a wire that carries sensor signal 16 from sensor electrical components to controller electrical components. In other alternative embodiments, controller 12 may have its own housing or may be included in a supplemental device. In yet other alternative embodiments, controller 12 may be co-located with an infusion device and a sensor system within a single housing. In further alternative embodiments, a sensor, a controller, and/or infusion communication systems may utilize a cable, a wire, a fiber optic line, RF, IR, or ultrasonic transmitters and receivers, combinations thereof, and/or the like instead of electrical traces, just to name a few examples.

Figure 2:
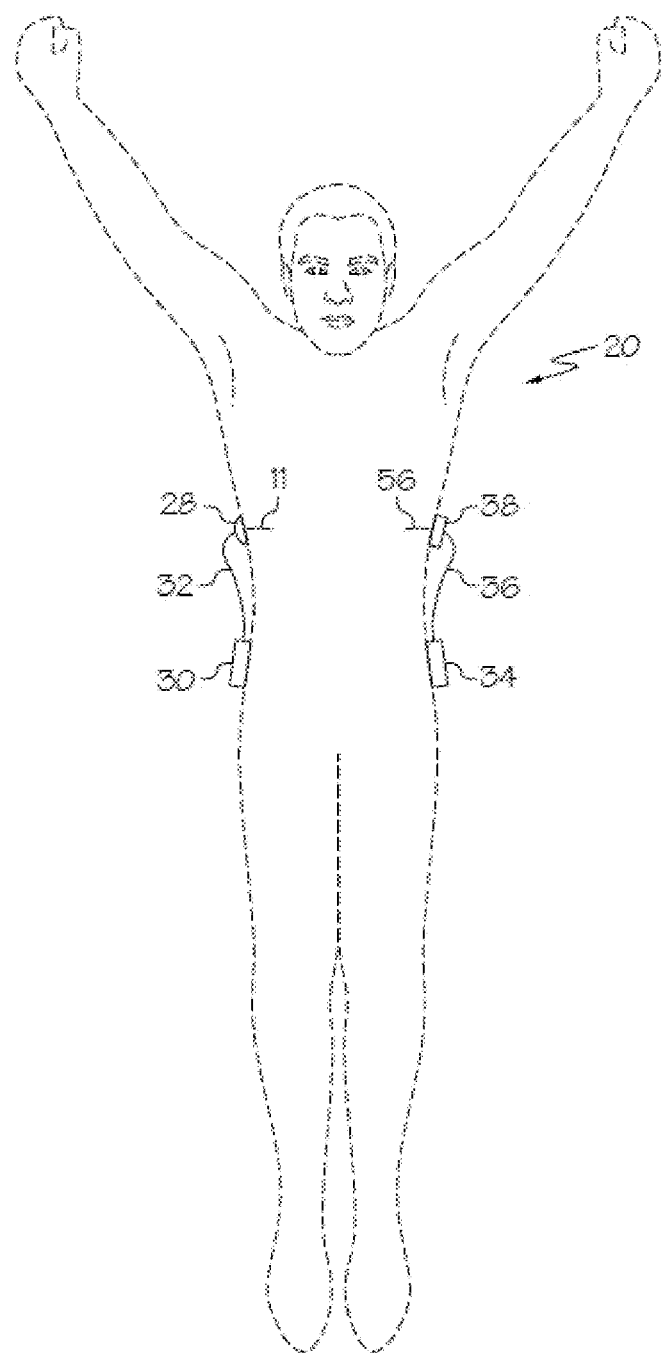
FIG. 2 is a front view of an analyte monitoring apparatus located on a body in accordance with an embodiment.

FIG. 2 illustrates an analyte monitoring apparatus in accordance with an embodiment. Such an analyte monitoring apparatus may be used, for example, in controlling a patient's glucose level about a target range as discussed above. It should be understood, however, that these are merely examples that may be used for controlling a patient's glucose level about a target range and that claimed subject matter is not limited in this respect. FIG. 2 is a front view of closed loop hardware located on a body in accordance with certain embodiments.

Particular embodiments may include a sensor 11, a sensor set 28, a telemetered characteristic monitor 30, a sensor cable 32, an infusion device 34, an infusion tube 36, and an infusion set 38, any or all of which may be worn on a body 20 of a user or patient, as shown in FIG. 2. Embodiments of a telemetered characteristic monitor 30 may include a monitor housing that supports a printed circuit board, battery or batteries, antenna a sensor cable connector, and so forth. A sensing end of sensor 11 may have exposed electrodes that may be inserted through skin to a sensor placement site such as into a subcutaneous tissue of a user's body 20. Electrodes may be in contact with interstitial fluid (ISF) that is usually present throughout subcutaneous tissue.

Sensor 11 may be held in place by sensor set 28, which may be adhesively secured to a user's skin. Sensor set 28 may provide for a connector end of sensor 11 to connect to a first end of sensor cable 32. A second end of sensor cable 32 may connect to monitor 30. A power source, such as batteries, that may be included in a monitor housing to provide power for sensor 11 and electrical components on an associated printed circuit board. Electrical components may sample sensor signal 16 (e.g., of FIG. 1) and store digital sensor values (Dsig) in a memory. Digital sensor values Dsig may be periodically transmitted from a memory to controller 12, which may be included in an infusion device.

With reference to FIGS. 1 and 2, a controller 12 may process digital sensor values Dsig and generate commands 22 (e.g., of FIG. 1) for infusion device 34. Infusion device 34 may respond to commands 22 and actuate a plunger 48 that forces insulin 24 (e.g., of FIG. 1) out of a reservoir 50 that is located inside an infusion device 34. Glucagon may be infused from a reservoir responsive to commands 22 using a similar and/or analogous device (not shown). In alternative implementations, glucose may be administered to a patient orally.

In particular example embodiments, a connector tip of a reservoir may extend through an infusion device housing, and a first end of infusion tube 36 may be attached to the connector tip. A second end of infusion tube 36 may connect to infusion set 38 (e.g., of FIG. 2). With reference to FIG. 1, insulin 24 may be forced through infusion tube 36 into infusion set 38 and into body 20. Infusion set 38 may be adhesively attached to a user's skin. As part of infusion set 38, a cannula may extend through skin and terminate in subcutaneous tissue 4 to complete fluid communication between a reservoir and subcutaneous tissue of a user's body 20.

In exemplary alternative embodiments, as pointed out above, a system in particular implementations may be a part of a hospital-based glucose management system. Given that insulin therapy during intensive care has been shown to dramatically improve wound healing and reduce blood stream infections, renal failure, and polyneuropathy mortality, irrespective of whether subjects previously had diabetes (See, e.g., Van den Berghe G. et al. NEJM 345: 1359-67, 2001), particular implementations may be used in a hospital setting to control a blood glucose level of a patient in intensive care. In such alternative embodiments, because an intravenous (IV) hookup may be implanted into a patient's arm while the patient is in an intensive care setting (e.g., ICU), a closed loop glucose control may be established that piggy-backs off an existing IV connection. Thus, in a hospital or other medical-facility based system, IV catheters that are directly connected to a patient's vascular system for purposes of quickly delivering IV fluids, may also be used to facilitate blood sampling and direct infusion of substances (e.g., insulin, glucose, glucagon, etc.) into an intra-vascular space.

Certain examples of system and/or environmental delays are described herein. Ideally, a sensor and associated component(s) would be capable of providing a real time, noise-free measurement of a parameter, such as a blood glucose measurement, that a control system is intended to control. However, in real-world implementations, there are typically physiological, chemical, electrical, algorithmic, and/or other sources of time delays that may contribute to a sensor measurement lagging behind an actual present value. Also, as noted herein, such a delay may arise from, for instance, a particular level of noise filtering that is applied to a sensor signal. Such delays and/or time lags in obtaining sensor glucose measurements may ultimately affect closed-loop operation. Accordingly, and as discussed in greater detail below, feedback control mechanisms using various approaches by application of a predicted duration of a blood glucose level being outside of a target range to better address a patient's glycemic health.

Figure 3:
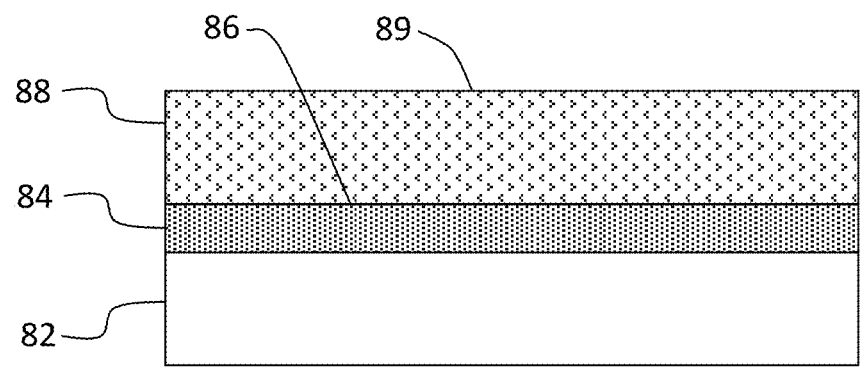
FIG. 3 is a cross sectional view of an analyte sensor for use in an analyte monitoring apparatus in an embodiment.

FIG. 3 illustrates a cross sectional of an exemplary sensor electrode 80, such as for use in an analyte monitoring apparatus. The sensor electrode 80 is formed from a plurality of components that are typically in the form of layers of various conductive and non-conductive constituents disposed on each other according to accepted methods.

The embodiment shown in FIG. 3 includes a base layer 82 to support the sensor electrode 80. The base layer 82 can be made of a material such as a polymeric substrate, which may be self-supporting or further supported by another material as is known in the art. The base layer 82 may be a non-toxic biocompatible polymer, such as silicone compounds, polyimides, biocompatible solder masks, epoxy acrylate copolymers, or the like. An exemplary base layer 82 is polyethylene terephthalate (PET), polyimide (PI), or a composite thereof.

The exemplary sensor electrode 80 includes a conductive layer 84 which is disposed over, and/or directly on and/or combined with the base layer 82. An exemplary conductive layer 84 is platinum. The base layer 82 and/or conductive layers 84 can be generated using many known techniques and materials. In certain embodiments, the electrical circuit of the sensor is defined by etching the disposed conductive layer 84 into a desired pattern of conductive paths. An electrically insulating layer may be formed around the conductive layers 84. For example, the electrically insulating layer may be a polymer coating, such as non-toxic biocompatible polymers such as silicone compounds, polyimides, biocompatible solder masks, epoxy acrylate copolymers, or the like.

As shown, the conductive layer 84 is exposed to open the conductive layers 84 to the external environment and to, for example, allow an analyte such as glucose to permeate the layers of the sensor electrode 80 and be sensed by the sensing elements. Specifically, the conductive layers 84 include an electrode surface 86.

In the configuration shown in FIG. 3, an analyte sensing layer 88 (which is typically a sensor chemistry layer, meaning that materials in this layer undergo a chemical reaction to produce a signal that can be sensed by the conductive layers) is formed over and/or is disposed on the exposed electrode surface 86. The analyte sensing layer 88 forms the sensor surface 89 where an analyte such as glucose may bind as described above.

Figure 4:
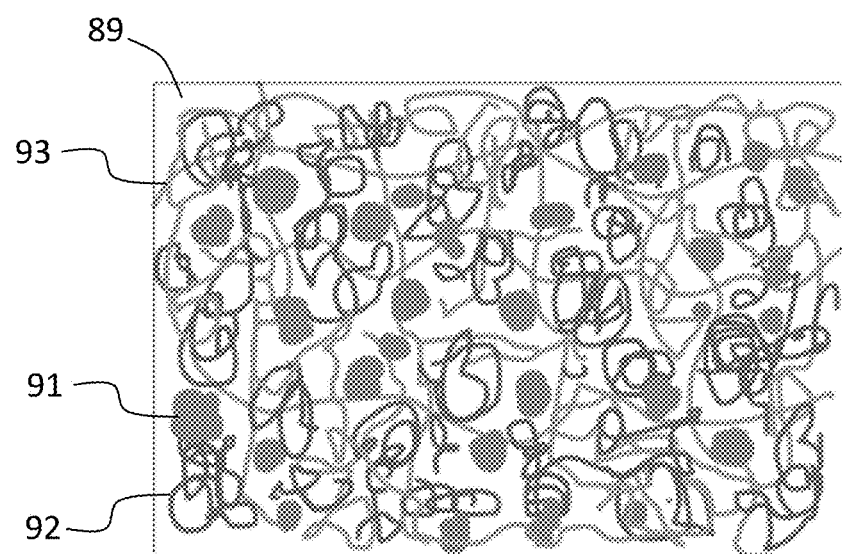
FIG. 4 is an overhead schematic view of the analyte sensing layer of the analyte sensor of FIG. 3 for an embodiment.

FIG. 4 provides an overhead schematic view of the analyte sensing layer 88. Cross-referencing FIGS. 3 and 4, it may be seen that the exemplary analyte sensing layer 88 includes an enzyme 91. Further, the exemplary analyte sensing layer 88 includes a thermally-cured polymer matrix 92 and a UV-cured polymer matrix 93. As shown, the enzyme 91 is entrapped within the matrix 92 and matrix 93.

An exemplary enzyme 91 is capable of producing and/or utilizing oxygen and/or hydrogen peroxide, for example, the enzyme glucose oxidase. In an illustrative embodiment, an oxidoreductase enzyme 91 such as glucose oxidase in the analyte sensing layer 88 reacts with glucose to produce hydrogen peroxide, a compound which then modulates a current at the electrode surface 86. As this modulation of current depends on the concentration of hydrogen peroxide, and the concentration of hydrogen peroxide correlates to the concentration of glucose, the concentration of glucose can be determined by monitoring this modulation in the current. In a specific embodiment, the hydrogen peroxide is oxidized at an electrode surface 86 that is an anode (also termed herein the anodic electrode), with the resulting current being proportional to the hydrogen peroxide concentration. Such modulations in the current caused by changing hydrogen peroxide concentrations can by monitored by any one of a variety of sensor detector apparatuses such as a universal sensor amperometric biosensor detector or one of the other variety of similar devices known in the art such as glucose monitoring devices produced by Medtronic MiniMed.

An exemplary method for forming the analyte sensing layer 88 provides a simplified process as compared to methods for forming conventional multi-layer sensing components. Specifically, the method includes mixing the enzyme 91, such as glucose oxidase, a polymer binder, a thermal cross-linker, an ultraviolet (UV) curable monomer or oligomer, a photo-initiator, such as a UV photo-initiator, and solvents to form a blended mixture or formulation. TABLE 1 provides an exemplary blended mixture before curing:

TABLE 1

| Component | Weight Percent (Wt. %) of total |
| --- | --- |
| Glucose Oxidase | 1-5 |
| PVA (polymer binder) | 2-10 |
| Glyoxal (thermal cross-linker) | 0.02-0.2 |
| Pentaerythritol Triacrylate (UV monomer or oligomer) | 5-15 |
| 1-Hydroxy-cyclohexyl-phenyl-ketone (UV photo-initiator) | 0.2-1.5 |
| DI-water, IPA, acetone (Solvent) | 68.3-91.78 |
| Total | 100 |

In an exemplary embodiment, the polymer binder has hydroxy end groups. An exemplary polymer binder is poly (vinyl alcohol) (PVA), hydroxypropyl methylcellulose (HPMC), chitosan, or other hydroxyl-containing polymers. Other suitable polymer binders may be used.

In an exemplary embodiment, the thermal cross-linker is glyoxal or glutaraldehyde. Other cross-linkers may be suitable.

In an exemplary embodiment, the monomer or oligomer includes multifunctional acrylate. Further, in exemplary embodiments, the multifunctional acrylate is selected from the group consisting of pentaerythritol triacrylate, dipentaerythritol pentaacrylate, ethoxylated pentaerythritol tetraacrylate, and multifunctional urethane acrylate monomers or oligomers.

An exemplary photo-initiator is adapted to initiate curing of the monomer or oligomer upon exposure to ultraviolet (UV) light. In an exemplary embodiment, the photo-initiator is selected from the group consisting of 1-Hydroxy-cyclohexyl-phenyl-ketone, 1,2-Diphenyl-2,2dimethyoxyethanone, and Bis(2,4,6-trimethylbenzoyl)-phenylphosphineoxide. Other photo-initiators may be suitable.

In an exemplary embodiment, the solvent is water, alcohol, ketone, acetate, or mixtures thereof.

After the blended mixture is formed, it may be coated onto a surface such as onto the electrode surface 86 of the conductive layer 84 to form a wet film. The blended mixture may be coated onto the surface by slot-die, gravure, knife coating, spray coating, curtain coating, dip coating, Mayer rod application, or other coating methods.

After application onto the surface, the wet film may be dried. For example, the wet film may be dried at a temperate of from about 40 to about 55° C. for a selected duration. For example, the wet film may be dried for from about 15 to about 30 minutes. During the drying process, thermal curing of the polymer binder and thermal cross-linker occurs. Further, during the drying process substantially all of the solvent may evaporate. In certain embodiments, the drying process may produce a dry film in which a portion of the solvent may remain unevaporated.

Then, the process may continue with exposing the dried film to UV light. Upon exposure to UV light, the monomer or oligomer is cured in the presence of a photo-initiator.

It has been found that by controlling ratio of the amount of polymer binder and monomer or oligomer (polymer binder:monomer-oligomer), the permeability of the analyte sensing layer 88 can be finely tuned to provide desired performance of the analyte sensor. For example, the ratio may be from about 1:10 to about 10:1.

In embodiments, the analyte sensing layer 88 can be applied over portions of the conductive layers or over the entire region of the conductive layers. Typically the analyte sensing layer 88 is disposed on the working electrode which can be the anode or the cathode. Optionally, the analyte sensing layer 88 is also disposed on a counter and/or reference electrode. While the analyte sensing layer 88 can be up to about 1000 microns (μm) in thickness, typically the analyte sensing layer is relatively thin as compared to those found in sensors previously described in the art, and is for example, typically less than about 100, less than about 50, less than about 25 or less than about 10 microns in thickness, and greater than about 1, greater than about 5, greater than about 10, or greater than about 25 microns in thickness.

Unlike conventional systems, the analyte sensing layer 88 is not coated and or disposed next to one or more additional layers, such as protein layers like human serum albumin, bovine serum albumin or the like, analyte modulating layers to regulate analyte contact with the analyte sensing layer 88, such as a glucose limiting membrane to regulates the amount of glucose that contacts an enzyme such as glucose oxidase that is present in the analyte sensing layer 88, interference rejection layers, or adhesion promoter layers disposed between such additional layers. Rather, the analyte sensing layer 88 performs by itself, with no additional layers, to regulate analyte contact, for example between glucose and glucose oxidase. Further, the analyte sensing layer 88 performs by itself, with no additional layers, to immobilize the enzyme therein.

Unless specifically stated otherwise, as is apparent from the preceding discussion, it is to be appreciated that throughout this specification discussions utilizing terms such as "processing", "computing", "calculating", "determining", "estimating", "selecting", "identifying", "obtaining", "representing", "receiving", "transmitting", "storing", "analyzing", "associating", "measuring", "detecting", "controlling", "delaying", "initiating", "setting", "delivering", "waiting", "starting", "providing", and so forth may refer to actions, processes, etc. that may be partially or fully performed by a specific apparatus, such as a special purpose computer, special purpose computing apparatus, a similar special purpose electronic computing device, and so forth, just to name a few examples. In the context of this specification, therefore, a special purpose computer or a similar special purpose electronic computing device or apparatus may be capable of manipulating or transforming signals, which are typically represented as physical electronic and/or magnetic quantities within memories, registers, or other information storage devices; transmission devices; display devices of a special purpose computer; or similar special purpose electronic computing device; and so forth, just to name a few examples. In particular embodiments, such a special purpose computer or similar may include one or more processors programmed with instructions to perform one or more specific functions. Accordingly, a special purpose computer may refer to a system or a device that includes an ability to process or store data in the form of signals. Further, unless specifically stated otherwise, a process or method as described herein, with reference to flow diagrams or otherwise, may also be executed or controlled, in whole or in part, by a special purpose computer.

It should be noted that although aspects of the above apparatuses, methods, sensors, devices, processes, etc. have been described in particular orders and in particular arrangements, such specific orders and arrangements are merely examples and claimed subject matter is not limited to the orders and arrangements as described. It should also be noted that systems, devices, methods, processes, etc. described herein may be capable of being performed by one or more computing platforms. In addition, instructions that are adapted to realize methods, processes, etc. that are described herein may be capable of being stored on a storage medium as one or more machine readable instructions. If executed, machine readable instructions may enable a computing platform to perform one or more actions. "Storage medium" as referred to herein may relate to media capable of storing information or instructions which may be operated on, or executed by, one or more machines (e.g., that include at least one processor). For example, a storage medium may include one or more storage articles and/or devices for storing machine-readable instructions or information. Such storage articles and/or devices may include any one of several non-transitory media types including, for example, magnetic, optical, semiconductor, a combination thereof, or other storage media. By way of further example, one or more computing platforms may be adapted to perform one or more processes, methods, etc. in accordance with claimed subject matter, such as methods, processes, etc. that are described herein. However, these are merely examples relating to a storage medium and a computing platform and claimed subject matter is not limited in these respects.

Although what are presently considered to be example features have been illustrated and described, it will be understood by those skilled in the art that various other modifications may be made, and equivalents may be substituted, without departing from claimed subject matter. Additionally, many modifications may be made to adapt a particular situation to the teachings of claimed subject matter without departing from central concepts that are described herein. Therefore, it is intended that claimed subject matter not be limited to particular examples disclosed, but that such claimed subject matter may also include all aspects falling within the scope of appended claims, and equivalents thereof.

What is claimed is:

1. A method for fabricating an analyte sensor, the method comprising the steps of:
   providing a base layer;
   forming a conductive layer over the base layer; and
   forming an analyte sensing layer disposed over the conductive layer,
      wherein the analyte sensing layer comprises glucose oxidase entrapped within a thermally-cured polymer matrix and within a UV-cured polymer matrix,
      wherein the thermally-cured polymer matrix is formed by thermally-curing a polymer binder and a thermal cross-linker,
      wherein the UV-cured polymer matrix is formed by UV-curing a monomer or an oligomer and a photo-initiator, wherein the monomer or the oligomer includes a multifunctional acrylate selected from the group consisting of pentaerythritol triacrylate, dipentaerythritol pentaacrylate, ethoxylated pentaerythritol tetraacrylate, and multifunctional urethane acrylate, and wherein forming the analyte sensing layer comprises UV-curing the monomer or the oligomer in the presence of the photo-initiator to form the UV-cured polymer matrix.

2. The method of claim 1, wherein forming the analyte sensing layer disposed over the conductive layer comprises:

thermally-curing the polymer binder and the thermal cross-linker to form the thermally-cured polymer matrix; and after forming the thermally-cured polymer matrix, UV-curing the monomer or the oligomer in the presence of the photo-initiator to form the UV-cured polymer matrix.

3. The method of claim 1, wherein forming the analyte sensing layer comprises combining the glucose oxidase, the polymer binder, the thermal cross-linker, the monomer or the oligomer, the photo-initiator, and a solvent to form a formulation.

4. The method of claim 3, wherein forming the analyte sensing layer further comprises coating the formulation onto the conductive layer.

5. The method of claim 1, wherein forming the analyte sensing layer further comprises thermally-curing the polymer binder and the thermal cross-linker by drying the formulation at a temperature within a range from about 40° C. to about 55° C.

6. The method of claim 1, wherein forming the analyte sensing layer further comprises UV-curing the monomer or the oligomer in the presence of the photo-initiator by exposing the formulation to UV light.

7. The method of claim 1, wherein the polymer binder has a hydroxyl end group.

8. The method of claim 1, wherein the polymer binder is selected from the group consisting of poly(vinyl alcohol) (PVA), hydroxypropyl methylcellulose (HPMC), chitosan, and hydroxyl-containing polymers.

9. The method of claim 1, wherein the thermal cross-linker is glyoxal or glutaraldehyde.

10. The method of claim 1, wherein the photo-initiator is selected from the group consisting of 1-Hydroxycyclohexyl-phenyl-ketone, 1,2-Diphenyl-2,2-dimethoxyethanone, and Bis(2,4,6-trimethylbenzoyl)-phenylphosphine oxide.

11. The method of claim 3, wherein the solvent is selected from the group consisting of water, alcohol, ketone, and acetate.

12. The method of claim 1, wherein a ratio of the polymer binder to the monomer or the oligomer is within a range from about 1:10 to about 10:1, and wherein the ratio is configured to control a permeability of the analyte sensing layer to regulate contact between glucose and the glucose oxidase.

13. The method of claim 1, wherein the base layer is a polyethylene terephthalate (PET), polyimide (PI) composite and the conductive layer is platinum.

14. The method of claim 1, wherein forming the conductive layer over the base layer comprises forming the conductive layer directly on the base layer, and wherein forming the analyte sensing layer disposed over the conductive layer comprises forming the analyte sensing layer directly on the conductive layer.

15. A method for fabricating an analyte sensing layer, the method comprising:

blending an enzyme, a polymer binder, a thermal cross-linker, a photo-initiator, and a monomer or an oligomer including a multifunctional acrylate selected from the group consisting of pentaerythritol triacrylate, dipentaerythritol pentaacrylate, ethoxylated pentaerythritol tetraacrylate, and multifunctional urethane acrylate to form a mixture;

thermally-curing the polymer binder and the thermal cross-linker by drying the mixture to form an intermediate film with a thermally-cured polymer matrix; and UV-curing the photo-initiator and the monomer or the oligomer including the multifunctional acrylate by exposing the intermediate film to UV light to form a UV-cured polymer matrix, wherein the enzyme is entrapped within the thermally-cured polymer matrix and within the UV-cured polymer matrix.

16. The method of claim 15, wherein the method further comprises, before thermally-curing the polymer binder and the thermal cross-linker, coating the mixture onto a surface of a conductive layer.

17. The method of claim 15, wherein the method further comprises blending a solvent with the enzyme, the polymer binder, the thermal cross-linker, the photo-initiator, and the monomer or the oligomer including the multifunctional acrylate to form the mixture.

18. The method of claim 17, wherein the enzyme is glucose oxidase.

19. The method of claim 15, wherein the polymer binder has a hydroxyl end group and is selected from the group consisting of poly(vinyl alcohol) (PVA), hydroxypropyl methylcellulose (HPMC), chitosan and hydroxyl-end group containing polymers.

20. The method of claim 15, wherein the thermal cross-linker is glyoxal or glutaraldehyde.

21. The method of claim 15, wherein the photo-initiator is selected from the group consisting of 1-Hydroxycyclohexyl-phenyl-ketone, 1,2-Diphenyl-2,2-dimethoxyethanone, and Bis(2,4,6-trimethylbenzoyl)-phenylphosphine oxide.

* * * * *